US008779391B2

(12) United States Patent
Flaherty et al.

(10) Patent No.: US 8,779,391 B2
(45) Date of Patent: Jul. 15, 2014

(54) STERILIZATION SYSTEM WITH ULTRAVIOLET EMITTER FOR ERADICATING BIOLOGICAL CONTAMINANTS

(75) Inventors: Patrick Flaherty, Bettendorf, IA (US); Bruce L. Winkler, Madison, WI (US); Robert J. Gold, Jackson Heights, NY (US)

(73) Assignee: Teckni-Corp, Bettendorf, IA (US)

( * ) Notice: Subject to any disclaimer, the term of this patent is extended or adjusted under 35 U.S.C. 154(b) by 128 days.

(21) Appl. No.: 13/404,781

(22) Filed: Feb. 24, 2012

(65) Prior Publication Data
US 2012/0223216 A1 Sep. 6, 2012

Related U.S. Application Data

(60) Provisional application No. 61/464,362, filed on Mar. 3, 2011.

(51) Int. Cl.
*G01N 21/64* (2006.01)
*A61L 2/24* (2006.01)
*A61L 2/10* (2006.01)
*G05D 1/02* (2006.01)

(52) U.S. Cl.
CPC .............. *A61L 2/24* (2013.01); *A61L 2202/25* (2013.01); *A61L 2202/14* (2013.01); *A61L 2202/16* (2013.01); *A61L 2/10* (2013.01); *G05D 1/0242* (2013.01); *G05D 2201/0203* (2013.01); *A47L 2201/04* (2013.01); *A47L 2201/06* (2013.01)
USPC ...................... 250/461.1; 250/461.2; 250/372; 15/339

(58) Field of Classification Search
USPC ................. 250/461.1, 461.2, 372; 15/339
See application file for complete search history.

(56) References Cited

U.S. PATENT DOCUMENTS

| 4,907,316 | A  | * | 3/1990  | Kurz ............................... 15/319 |
| 7,251,853 | B2 | * | 8/2007  | Park et al. ....................... 15/319 |
| 7,836,548 | B2 | * | 11/2010 | Cho .................................. 15/421 |
| 8,029,739 | B2 | * | 10/2011 | Field et al. .................... 422/292 |
| 8,226,887 | B2 | * | 7/2012  | Harmon et al. ................. 422/24 |
| 8,330,121 | B2 | * | 12/2012 | Douglas .................. 250/455.11 |
| 2004/0244138 | A1 | * | 12/2004 | Taylor et al. .................... 15/319 |
| 2007/0209143 | A1 | * | 9/2007  | Choi et al. ....................... 15/339 |

(Continued)

FOREIGN PATENT DOCUMENTS

JP 07008541 A * 1/1995

*Primary Examiner* — Christine Sung
(74) *Attorney, Agent, or Firm* — Charles S. Sara, Esq.; DeWitt Ross & Stevens SC

(57) ABSTRACT

An exemplary sterilization system includes a self-propelled robotic mobile platform for locating and eradicating infectious bacterial and virus strains on floors (and objects thereon), walls, cabinets, angled structures, etc., using one or more ultraviolet light sources. A controller allows the system to adjust the quantity of ultraviolet light received by a surface by, for example, changing the intensity of energy input to a ultraviolet light source, changing a distance between a ultraviolet light source and a surface being irradiated, changing the speed/movement of the mobile platform to affect time of exposure, and/or by returning to contaminated areas for additional passes. The mobile platform may include a sensor capable of detecting fluorescence of biological contaminants irradiated with ultraviolet light to locate contaminated areas. The system is thus capable of "seek and destroy" functionality by navigating towards contaminated areas and irradiating those areas with ultraviolet light accordingly.

18 Claims, 10 Drawing Sheets

(56) References Cited

U.S. PATENT DOCUMENTS

| | | | |
|---|---|---|---|
| 2008/0253941 A1* | 10/2008 | Wichers et al. | 422/186.3 |
| 2008/0295271 A1* | 12/2008 | Perunicic | 15/246.3 |
| 2009/0184268 A1* | 7/2009 | Garcia et al. | 250/504 R |
| 2010/0104471 A1* | 4/2010 | Harmon et al. | 422/24 |
| 2011/0214686 A1* | 9/2011 | Chavana et al. | 134/1 |

* cited by examiner

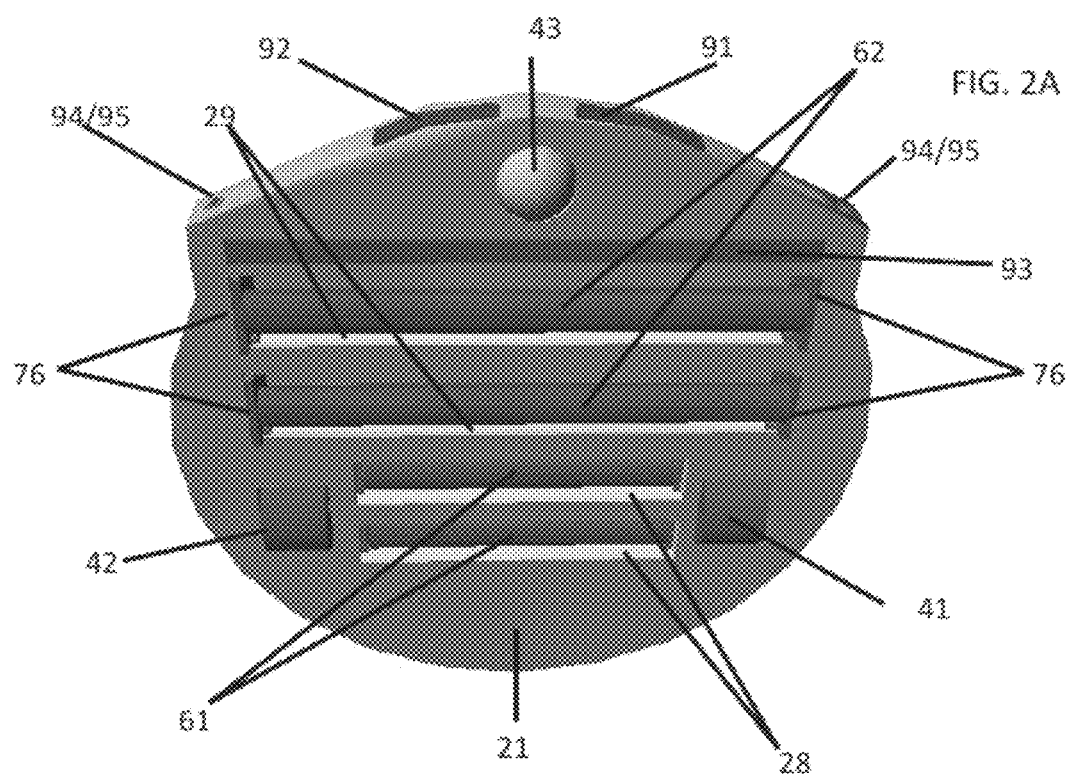
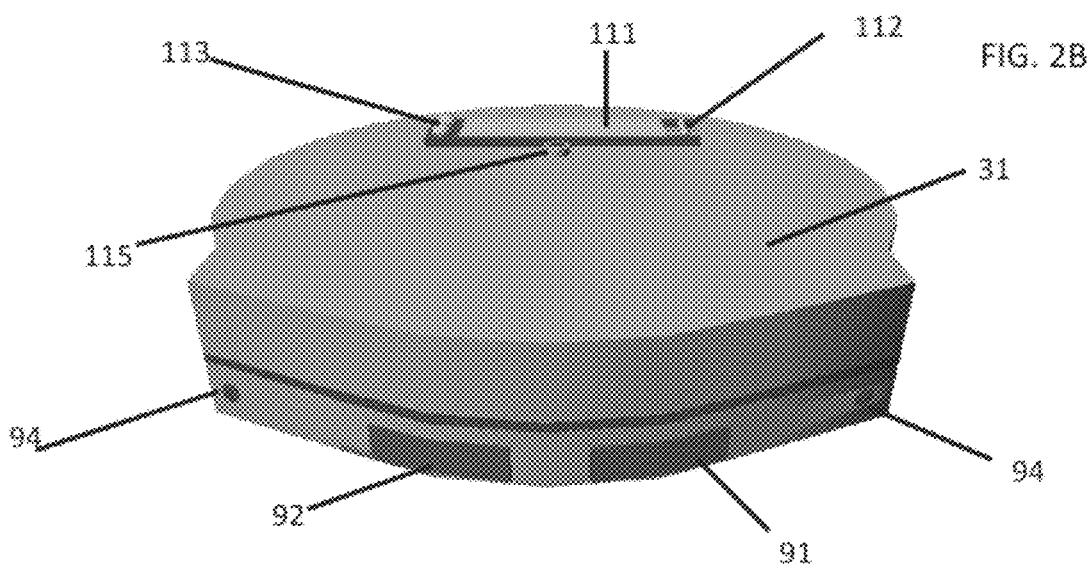
FIG. 2

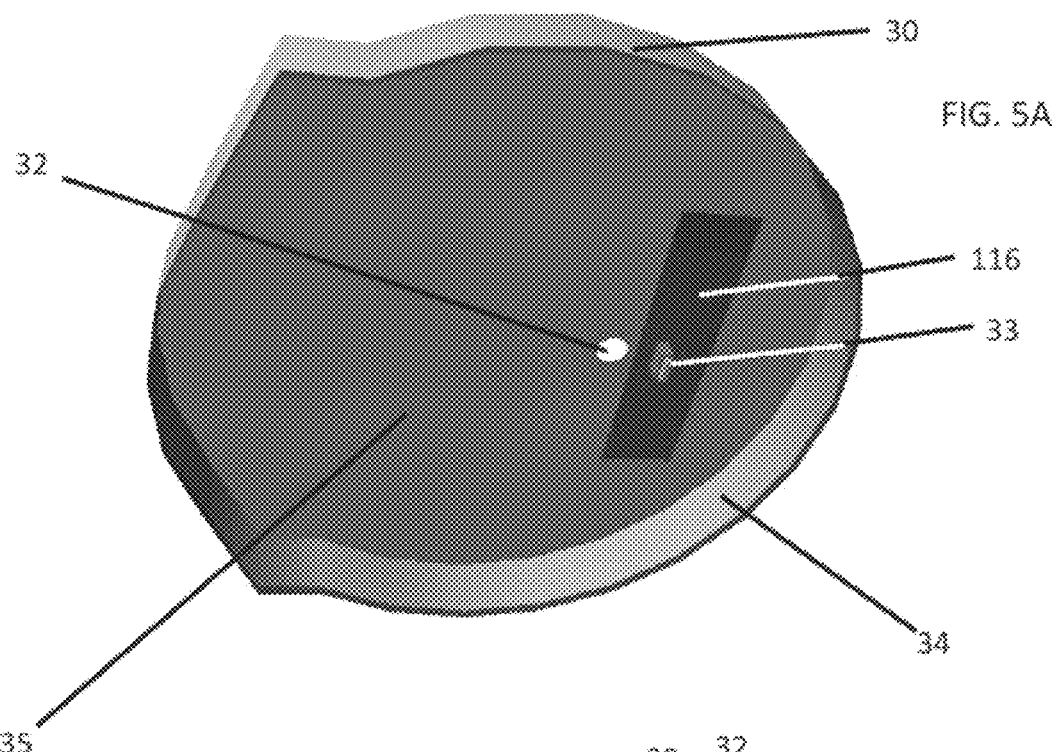
FIG. 5A
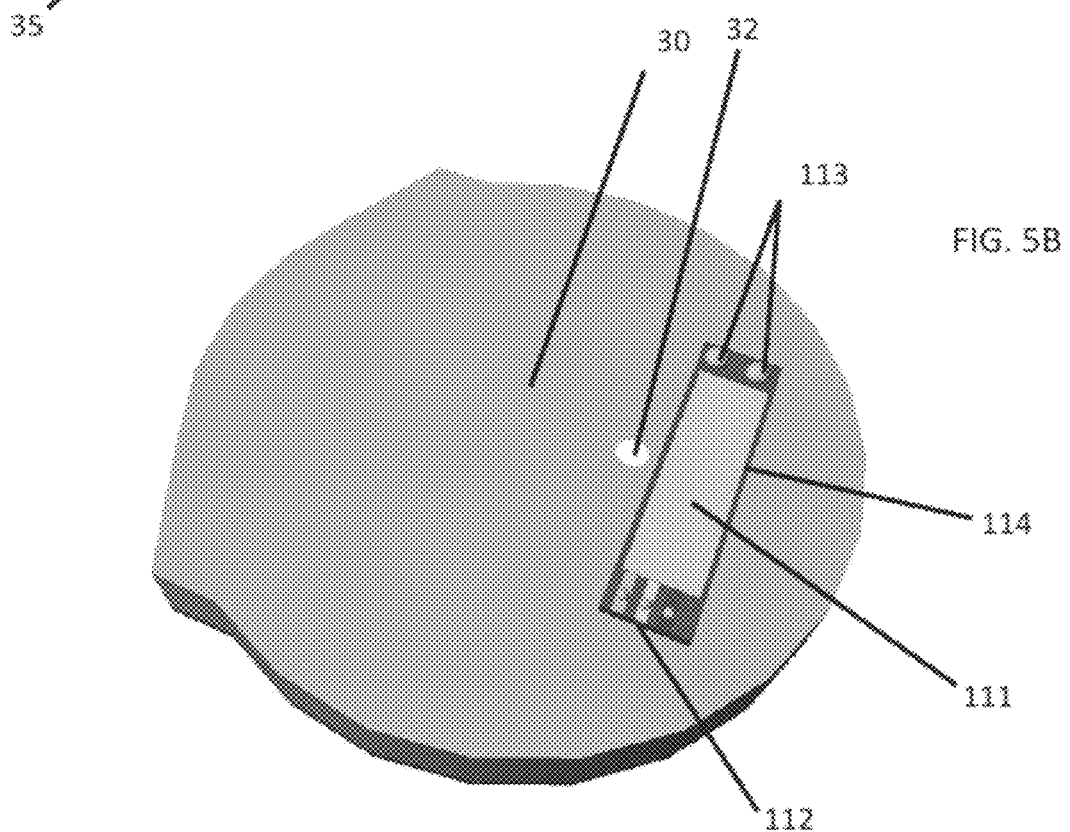
FIG. 5B
FIG. 5

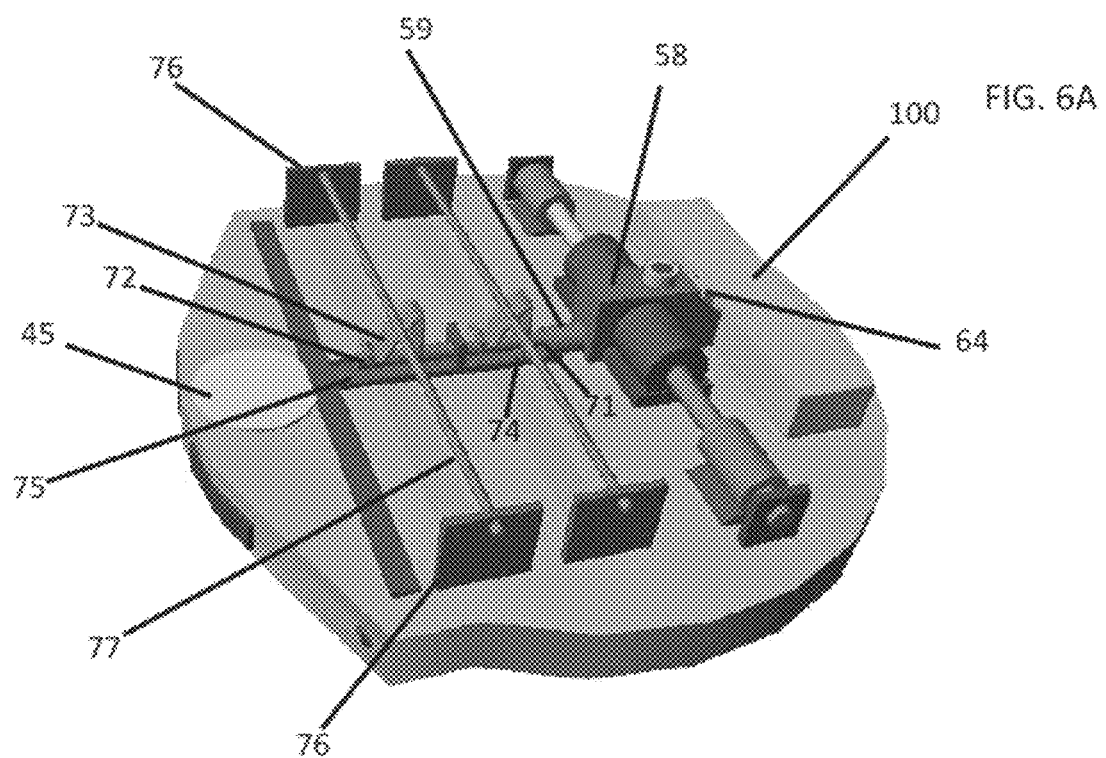
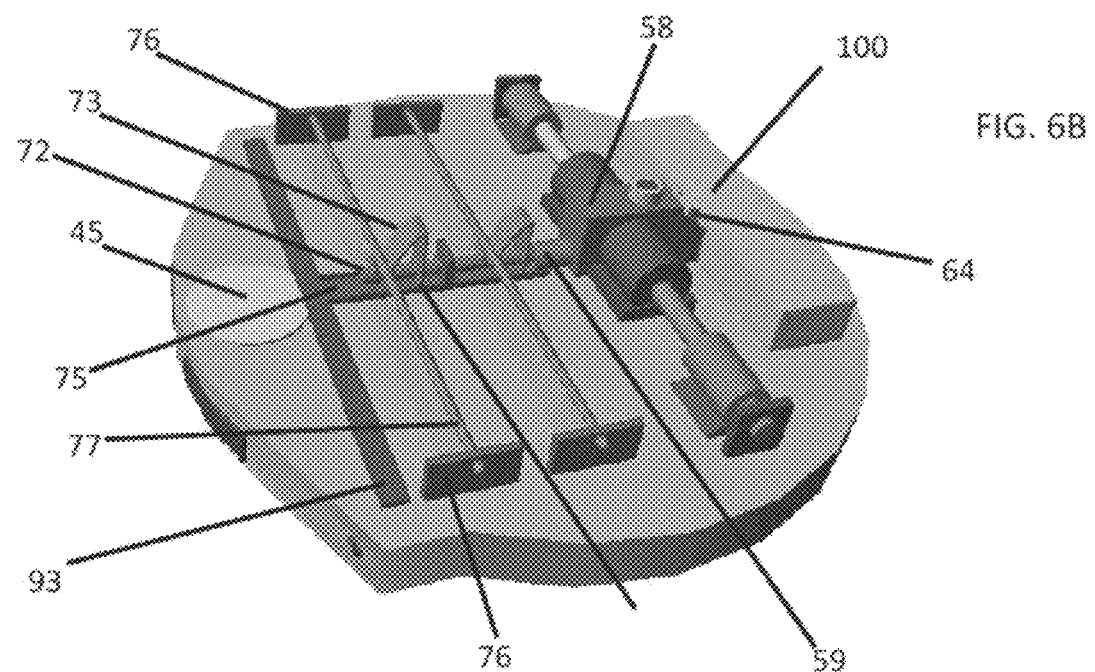
FIG. 6

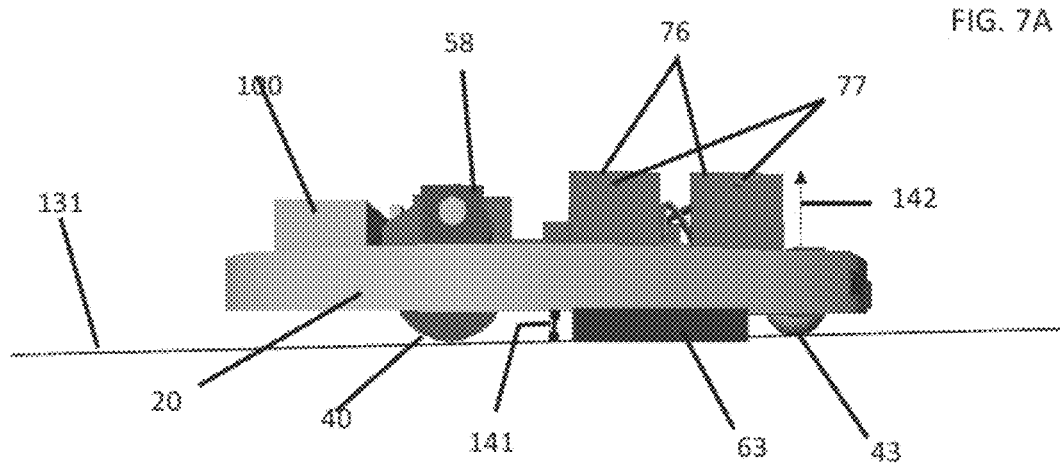
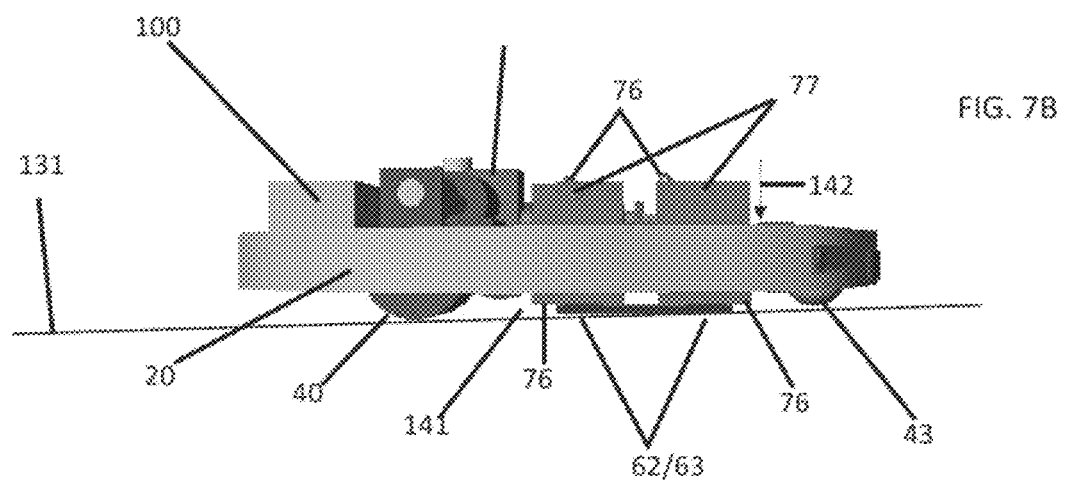
FIG. 7

STERILIZATION SYSTEM WITH ULTRAVIOLET EMITTER FOR ERADICATING BIOLOGICAL CONTAMINANTS

CROSS-REFERENCE TO RELATED APPLICATIONS

This application claims priority under 35 USC §119(e) to U.S. Provisional Patent Application 61/464,362 filed Feb. 24, 2011, the entirety of which is incorporated by reference herein.

FIELD OF THE INVENTION

Exemplary versions of the invention relate generally to self-contained devices created for the eradication of biological microorganisms and contaminants found on surfaces in public and private places, such as, for example, gymnasiums (such as gym floors and athletic floor mats), schools, daycares, hospitals, government buildings, homes, etc. Additionally, versions of the invention relate to a self-propelled, autonomous, robotic system which utilizes ultraviolet (UV) light as its eradication technology for the sterilization of infectious bacterial and virus strains on surfaces. Moreover, versions of the invention relate to a robotic device which utilizes sensors in conjunction with an internal computer logic system to both navigate a surface in a pre-programmed pathway or utilize an on-board sensor system to act autonomously to sense, locate, home-in on, and navigate to, areas of biological contaminants on a floor surface on which the robotic device is operating. Further, versions of the invention relate to a robotic self-guided platform which carries one or more UV light emission systems and associated control electronics and physical hardware which can be controlled via integral onboard computer logic to manipulate both the on-board physical mechanisms and electronics to autonomously accomplish the goal of the eradication of infectious bacterial and virus strains on adjacent surfaces in the most time- and energy-efficient manner. Furthermore, versions of the invention use UV light to eradicate infectious bacterial and virus strains via the manipulation of the strength of the UV light emission projected on the biological contaminants, the time of exposure of the UV light emission on the biological contaminants, and/or the distance of the UV light source from the biological contaminants at the time of exposure. Furthermore, versions of the invention relate to a robotic device which uses optical sensors and one or more projected low intensity UV lights to expose, identify, locate and help navigate to, biological contaminants on floor surfaces. Furthermore, versions of the invention are physically configured to include a structure having additional UV light sources which can be positioned to allow the eradication of biological contaminants on objects located on and above the floor level on which the structure is operating.

BACKGROUND OF THE INVENTION

In recent years, infectious bacterial and virus strains have become more common and a growing threat to the general public. This is true especially in third world countries, but amazingly the same threat faces almost every school gymnasium, private workout gym, hospital, school and business in all major countries. Private companies, public schools, hospitals and governments in general do not have the equipment, staff or tools to handle or effectively combat these kinds of bacterial and virus attacks. Surfaces shared by multiple families or children, who are often sweating from an illness, heat and/or exercise, end up sharing and spreading the contaminated biological materials from skin-to-skin and skin-to-contaminated-surface contact. Added to this are all types of adults, young adults and children who will leave to use the bathrooms in every type of school, gymnasium, home and business environment, and bring back additional bacterial contaminants on their shoes. As the primary play area for most children is the floor beneath their feet, the floor of many locations from kindergartens to daycare facilities to hospitals is often ripe with biological contaminants. As the various locations of surface-based infectious bacteria and viruses proliferate, especially shared exercise locations having mats and other floor surfaces where people come in contact with an ever changing bio-environment, the problem exists of how to effectively clean these surfaces in an effective, quick, repeatable and cost effective manner.

Commercial home-based robotic cleaning systems on the market today are intended for hard surfaces. But existing cleaning systems do not have the technology to eradicate infectious bacterial and virus strains effectively, or as a matter of routine, in the performance of their basic functions. This is mostly due to the fact that their design does not incorporate specific chemical or photonic emission devices whose chemical or wavelength parameters have been proven to effectively eradicate infectious bacterial and virus strains. Robotic cleaners having a vacuum system or even a mopping system do little or nothing against these infectious bacterial and virus strains. In fact, the mopping action of some systems can actually spread a contagion past its initial location to other sections of a floor surface and into the cleaning device itself. The use of chemicals (which may be harsh/unsafe and/or environmentally-unfriendly) in some of these mopping devices could limit the spread of contagion, but manufacturers have shied away from this approach because it would mean both a constant monitoring and reloading of chemicals into these devices to keep them effective, and the fact that the effective application of the chemicals on the desired floor or mat surfaces does not always provide 100-percent coverage or protection against the infectious bacterial and virus strains. What is needed is a device that utilizes a non-contact technology, such as UV light to disrupt the DNA structures within bacteria and virus, thus effectively eradicating these biological contaminants.

SUMMARY OF THE INVENTION

Exemplary versions of the invention generally relate to a self-propelled system for sterilizing surfaces which may utilize a multi-axis two-dimension mobile robotic platform housing one or more high-intensity UV light sources as the eradication technology for the sterilization of infectious bacterial and virus strains on floors, exercise mats, and other surfaces. Ultraviolet light can be used to kill different kinds of bacteria strains based on the intensity of the light used, the exposure time to the bacteria, and the distance from the bacteria.

The sterilization system can be wall-charged within a given operating environment, but can also be exclusively battery and/or solar powered, or a combination of the three. The robotic unit may incorporate an integral, large UV light emitter, or an array of several smaller bulbs, that can be controlled for intermittent or continuous operation, and that can sterilize large areas automatically as the robotic unit passes over a surface. The sterilization system can be used daily, or as often as needed, at any location to perform multiple pre-programmed or autonomous passes over any desired surface area to kill targeted dangerous virus and bacteria contamination. These timed and regularly scheduled "patrols" or "as needed" activation of the robotic unit to pass over floor surfaces that need to kept free of infectious bacterial and virus strains will significantly improve the sanitation, health, and safety of family facilities, food service areas, hospitals, multiple living dwellings and other facilities where people regularly gather. The use of the sterilization system in this automatic and regularly scheduled format, or as needed by circumstance, provides the ability to clean infectious bacterial and virus strains from facilities where the need to sterilize floors is critical, and could clean these surfaces with little danger to human operators due to its automated and robotic nature.

Optionally, the sterilization system can utilize a current COTS (commercial off-the-shelf technology) robot chassis with a design that is capable of carrying out its specific mission, but without the added weight and clutter associated with the interior mechanism of a robotic vacuum or mopping device. That is, the sterilization system can utilize an existing robotic chassis with navigation systems technology and sensors that are capable of both pre-programmed patterns and "edge detection" capability to patrol designated areas. The robotic chassis can be equipped with outward-looking low-powered UV "headlamps" with a longer range projection capability, which operate as a "target designator" for the navigation system. In the role of target designator for the sterilization system, these lower powered UV headlights can cause biological contaminants on surfaces around the sterilization system (and in the path of the headlights) to illuminate due to, for example, the effect of UV light causing fluorescence of biological contaminants. The biological contaminants might also be detected by, for example, illumination or other change in appearance due to the manner in which the contaminants refract/reflect/absorb other light (such as "black light"). Such illumination/fluorescence/change in appearance could be detected using the sterilization system's integral photonic sensors (or other sensors) and the navigation system can be programmed (in one of various on-board program modes) to seek out these illuminated areas and cleanse them of their infectious bacterial and virus strains. The amount and size of the various biological contaminants that may be picked up by the sterilization system sensors can correlate to the speed at which the unit will pass over the area of the biological contaminants. The slower the motion over the biological contaminants, the more intense the amount of cleansing UV photons that are on the targeted area under the robotic unit. With the intensity of the optical sensor feedback-correlated against the integral logic database of "time on target" (TOT) for effective decontamination, the sterilization system will be able to effectively eradicate the biological contaminant, often using single passes over an area. This will reduce the need for multiple sweeps to effectively clean a floor or mat surface.

The sterilization system integral logic system can also adjust the drive motor in a forward or backward motion in conjunction with rearward looking sensors mounted on the robotic platform. The rearward looking UV illuminator and sensor could observe the area just coming out from under the robotic platform decontamination sweep zone in the wake of the robotic platform motion. If the rearward looking sensors detect, via (for example) the fluorescence effect or other illumination, the remains of any biological contaminants in its rear path, it can automatically stop and back up over the area again, even doing multiple passes until the area of this very strong biological contaminant is clean of infectious bacterial and virus strains.

The sterilization system could utilize its integral logic protocols to apply power to the drive motors in a manner that effectively directs and applies the proper time-on-target—via speed control and the ability to make multiple passes on a location while still maintaining its overall full patrol area directives to any pre-set patrol pattern. The ability to detect areas of special concern, based upon sensor feedback parameters, can be pre-set or set by the user within the sterilization system integral logic system.

The sterilization system could utilize multiple types of operational controls to make sure that very high contamination areas are UV-irradiated at a level and timeframe that is warranted by the sensor feedback to the sterilization system's integral logic system. The sterilization system will use a direct control over the UV-C bulb intensity, in coordinated combination with the speed of the unit and the sensor feedback, so that a logic matrix within the sterilization system's integral logic system can decide the best use of available on-board energy reserves to best use either multiple passes or higher UV-C light intensity, or a combination of the two to achieve its directive of the eradication of biological contaminants.

The sterilization system could use multiple types of operational controls to make sure that regular and high contamination areas are UV irradiated at a level and timeframe that is warranted by the sensor feedback to the sterilization system's integral logic system. The sterilization system could use a direct control over a simple mechanical height adjustment of the vertical position of the UV-C light emitting bulbs so that a range of distances is achievable between the UV-C bulbs and the biological contaminants on the surface below the bulbs. Less distance creates a higher rate of eradication of the biological contaminants exposed to the UV-C light. The sterilization system can use the logic matrix within the integral logic system to decide the best use of available on-board energy reserves to best use either multiple passes, higher UV-C light intensity, or a change in the operational distance of the UV-C bulb to the biological contaminants, or any combination of the three sub-systems to achieve the best outcome in fulfilling its directive of the eradication of biological contaminants within its area of operation.

The combination of at least four distinct variables—[1] the UV-C bulb intensity; [2] the speed at which the robotic platform moves across a surface; [3] the ability to change the height of the UV-C bulb in relation to the biological contaminant; and [4] the ability to reverse direction to re-apply UV-C emissions to a specific area by making additional passes—will allow the internal logic programming of the sterilization system to select its best option based upon time, energy reserves, and other programmable and pre-set variables so the sterilization system can effectively achieve its operational goals.

The sterilization system can be configured with additional UV-C light emitters on its top surface that can be aimed, on demand, at surfaces around and somewhat above the robotic platform while it is moving on a floor surface. In this manner, a sterilization system equipped in this fashion could use its navigational sensors to move around objects, such as children's toys on a floor of a low shelf area, and focus its attention—via, for example, its optical sensors detecting biological contaminants causing the scanning UV light coverage to cause an illumination on said objects—and then increase the intensity of the scanning lights upward so that their emissions are effective in the eradication of biological contaminants on the above surface objects. This optional facility of the sterilization system would enhance its operational capability and allow more protection to areas and objects that are not flush under the path of the sterilization system.

If there is a danger of unintentionally irradiating persons or animals, or other sensitive surfaces, the system could be operated "after hours" or in particular areas. Optionally, a motion sensor could be included to serve as a failsafe switch. That is, if motion is detected by the system in its vicinity, the system could be programmed to deactivate its UV light sources to minimize the risk of irradiating, for example, children or pets.

By using the integral logic system, in coordinated combination with the sensor feedback and the logic matrix within the integral logic system, the sterilization system can decide the best use of available on-board energy reserves to accomplish its mission without running out of power while away from its automatic re-charging station.

By optionally using current COTS, the sterilization system may benefit from components which are time-tested, power conservative, relatively inexpensive, easy to repair, and with available replacement parts. Such a sterilization system could provide a unique new biological protection device that utilizes proven sub-systems to accomplish a goal no other robotic cleaner has achieved thus far.

Accordingly, several objects and advantages of the sterilization system are described herein. In one exemplary version, the sterilization system provides for effective eradication of floor surface biological contaminants via the use of UV light sources as the means for the sterilization of surfaces on which the invention can travel from bacteria and viruses.

In another exemplary version, the sterilization system provides for the eradication of surface biological contaminants on objects at floor level, as well as objects that are above floor level (depending upon the capabilities of the actual UV-C emitters and other physical components selected for integration in the particular unit) via the sterilization of the infectious bacterial and virus strains on surfaces in the vicinity of the unit or surfaces with which the invention can otherwise interact.

In another exemplary version, the sterilization system uses UV-C light as a target designator of biological contaminants via the use of low power UV-C light "headlights" or "taillights" in conjunction with on-board optical sensors to detect levels of illumination around the sterilization system, and which can be used to both target the location of the biological contaminants and estimate the strength of the biological contaminants based upon their illumination, so that a proper combination of on-board eradication methodologies can be used to effectively sterilize and destroy the surface biological contaminants in the shortest timeframe and using the optimal energy resources within the invention.

Exemplary sterilization systems include self-contained robotic devices for the eradication of biological contaminants found on floor surfaces which use UV light emission technology in multiple distinct protocols, adjusting, for example: the time that the UV light will be directed against the targeted biological contaminants; the power applied to the UV emission emitter source to vary the intensity of the UV light that is directed against the biological contaminants; the distance of UV light sources from surfaces; the reversal of direction as needed to re-cover in multiple sweeps an area suspected of continued biological contamination; and/or the adjustment of the height of a UV bulb above targeted biological contaminants. This logic based control system which will be an integral part of the computer electronics of the sterilization system will manipulate such options as time-on-target, multiple sweeps over a target, intensity of emission against the target, and the distance from the targeted biological contaminants to provide the most effective and energy-efficient application of UV light to maximize sterilization.

Other exemplary sterilization systems may include a self-propelled and guided robotic system which utilizes UV light as its eradication technology for the sterilization of infectious bacterial and virus strains on surfaces adjacent to the area of emissions of the UV light source. Such sterilization systems can use one, or multiple, navigation systems which include pre-programmed "patrol" paths that sweep a defined area in a defined pattern; a sensor-guided navigation system which can utilize laser or sonar distance recognition and obstacle avoidance technology to guide the invention around a pre-determined border area; and/or a "targeting" navigation system which (in conjunction with laser or sonar obstacle avoidance capabilities) can utilize UV light and optical sensors to seek out and find biological contaminants which have a detectable illumination under projected low-intensity UV light or other light. The sensors can be used to guide the sterilization system to areas for the eradication of the detected infectious bacterial and/or virus strains that are present.

Exemplary versions include a robotic device which can utilize various sensory input from different types of sensors in conjunction with an internal logic system to both navigate a surface in a pre-programmed fashion or utilize its sensor system to sense and locate, home-in on, and navigate to, areas of biological contaminants on a floor surface on which the invention is operating.

The sterilization system's physical configuration can include structures that allow both the detection and eradication of biological contaminants on objects on and above the floor on which the invention is operating. This can be accomplished with multiple top-side UV emission sources (such as secondary UV light sources) that can be actively manipulated by the sterilization system's internal logic system in a manner that allows the projected UV light to be aimed at objects adjacent to and slightly above the invention (in its position on the floor surface) and allow both floor cleaning of biological contaminants and the cleansing of physical objects like toys that may be laying on the same floor surface but would not be under the primary UV light emitters of the sterilization system.

Further advantages and features of the invention will be apparent from the remainder of this document in conjunction with the associated drawings.

BRIEF DESCRIPTION OF THE DRAWINGS

FIGS. 2A and 2B depict perspective views of the bottom and top, respectively, of the exemplary sterilization system.

FIGS. 5A and 5B depict bottom and top views, respectively, of the exemplary sterilization system.

FIGS. 6A and 6B depict top perspective views of the main body of the exemplary sterilization system with sub-components in a position to raise and lower, respectively, the moveable UV lighting system.

FIGS. 7A and 7B depict side views of the main body of the exemplary sterilization system with sub-components in a position to raise and lower, respectively, the moveable UV lighting system.

Figure 1:
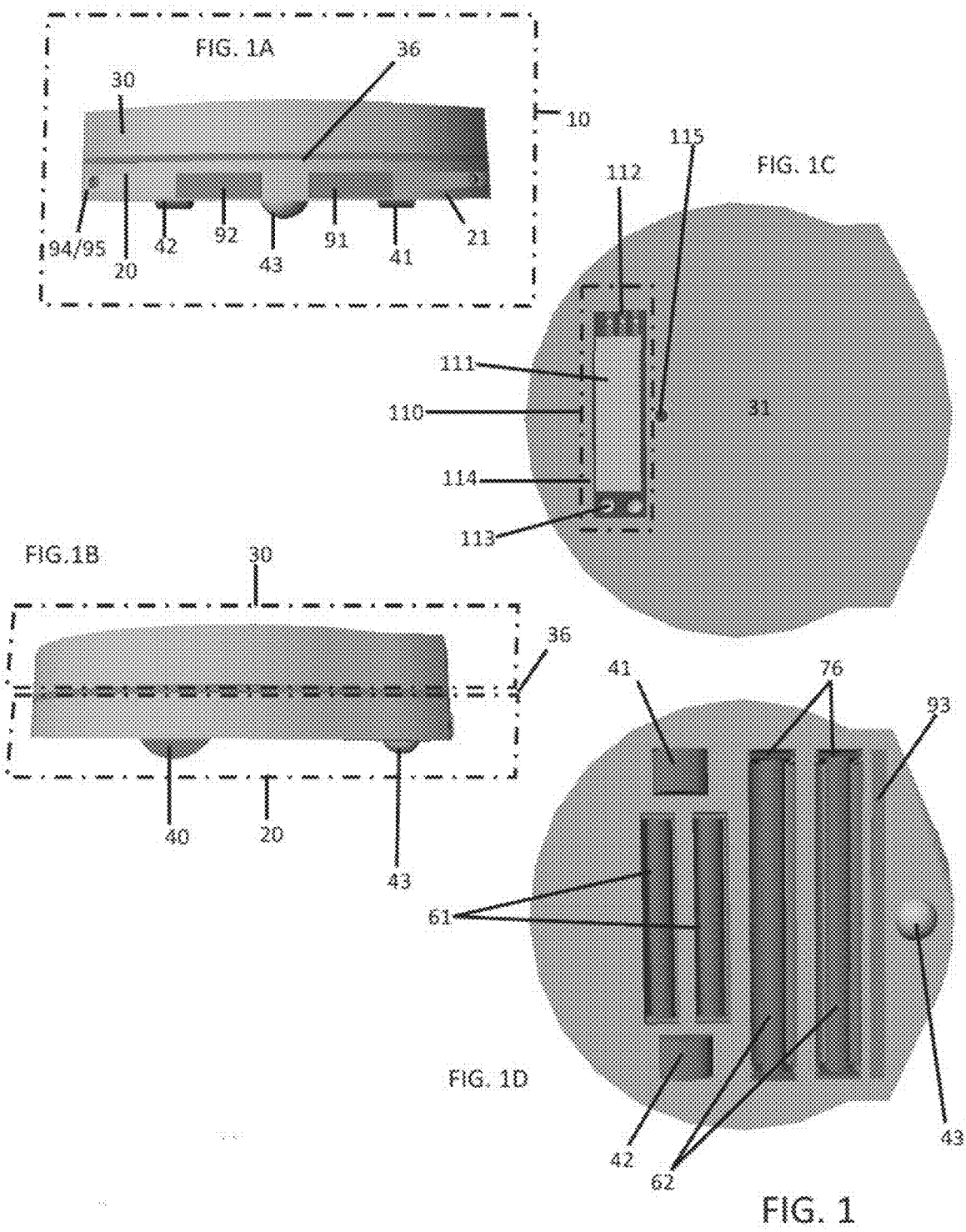
FIGS. 1A, 1B, 1C, and 1D depict front, side, top, and bottom views, respectively, of an exemplary sterilization system.

The following list identifies exemplary components shown in the above figures:

| | |
|---|---|
| 10. | Sterilization system |
| 11. | Front of exemplary sterilization system |
| 12. | Rear of exemplary sterilization system |
| 20. | Main Body |
| 21. | Bottom Surface (of Main Body) |
| 22. | Top Surface (of Main Body) |
| 23. | Ball Cavity |
| 24. | Battery Cavity |
| 25. | Wheel Wells |
| 26. | Light Height Adjustment Slots |
| 27. | Cavity (for Downward Looking Sensor) |
| 28. | Cavity (for Stationary UV Lights) |
| 29. | Cavity (for Adjustable Height UV Lights) |
| 30. | Top Cover |
| 31. | Top Surface (of Top Cover) |
| 32. | Pass through port (for On-Off Button) |
| 33. | USB Connector (Control Panel 110 to Computer Core 58) |
| 34. | Inside Wall (of Top Cover) |
| 35. | Interior Top Surface (of Top Cover) |
| 36. | Center line (between the two halves of the Sterilization system) |
| 40. | Wheels |
| 41. | Left Wheel |
| 42. | Right Wheel |
| 43. | Steering Ball |
| 44. | Wheel Shaft |
| 45. | Ball Cavity Cover |
| 50. | Motion Management System |
| 51. | Left Wheel Drive Motor |
| 52. | Right Wheel Drive Motor |
| 53. | Left Drive Shaft |
| 54. | Right Drive Shaft |
| 55. | Left Drive Drum |
| 56. | Right Drive Drum |
| 57. | Support Blocks |
| 58. | Computer Core |
| 59. | Step Motor |
| 60. | Main Lighting Components |
| 61. | Stationary UV Bulbs |

-continued

| | |
|---|---|
| 62. | Movable UV Bulbs |
| 63. | UV Light projection |
| 64. | USB Connector (from Computer Core to Control Panel) |
| 70. | UV Height Management System |
| 71. | Piston Port |
| 72. | Height Piston |
| 73. | Height Ramps |
| 74. | Guides (of Height Piston) |
| 75. | Guide Track (for Height Piston Guides) |
| 76. | Riser Guides (of Riser Rods) |
| 77. | Riser Rods |
| 78. | Riser Guide Sensor Slots |
| 80. | Wiring Harness |
| 90. | Sensors |
| 91. | Left Forward Looking Sensor/Illuminator |
| 92. | Right Forward looking Sensor/Illuminator |
| 93. | Downward Looking Sensor |
| 94. | Laser Range Finder |
| 95. | Laser Path Indicator |
| 96. | UV Sensor Beam Pattern |
| 97. | Low Level UV Forward Projected Light |
| 98. | Sensor Data |
| 100. | Battery |
| 101. | Battery Contacts |
| 102. | Battery Base |
| 110. | Control Panel |
| 111. | Screen |
| 112. | Status Indicators |
| 113. | Selector Buttons |
| 114. | Control Casing |
| 115. | Manual On-Off Button |
| 116. | Bottom (Control Panel) |
| 120. | Auxiliary Lighting System |
| 121. | Top Mounted UV Bulbs |
| 122. | Rotational Shields (for Top Mounted UV Bulbs) |
| 123. | Motorized Pivot |
| 124. | Bulb Support Structure |
| 125. | Upward Looking Sensor |
| 130. | Surfaces |
| 131. | Floor |
| 132. | Wall |
| 133. | Gym Mat |
| 134. | Vertical Edge |
| 135. | Horizontal Surface |
| 136. | Tilted Surface |
| 137. | Biological Contaminants |
| 138. | Fluorescence/Illumination |
| 139. | Microorganisms |
| 140. | Distances |
| 141. | Base Gap |
| 142. | Rise of UV Lights |
| 143. | Lowering of UV Lights |

DETAILED DESCRIPTION OF PREFERRED VERSIONS OF THE INVENTION

As seen in FIGS. 1A through 1D, an exemplary Sterilization system 10 has a lower half which is the Main Body 20 and an upper half which is the Top Cover 30. The two halves join at a center line 36 which allows the Top Cover 30 to hide and protect the interior components which reside in the Main Body 20 of the Sterilization system 10. On the top surface of the Top Cover 30 is the Control Panel 110. The Control Panel 110 is the main "command and control unit" of the Sterilization system 10 and is used to issue commands for the control of the basic functions of the Sterilization system 10.

The Control Panel 110 is connected to the Computer Core 58 of the Motion Management System 50 via a detachable electrical USB Connector 33. USB Connector 33, as shown in FIG. 5A, extends from the bottom 116 of the Control Panel 110 so that it inserts into the USB Connector 64 on the Motion Management System 50 component. The connection between the control Panel 110 and the Computer Core 58 can be by any type of extendable or dis-attachable electrical connection between the parts.

Figure 9:
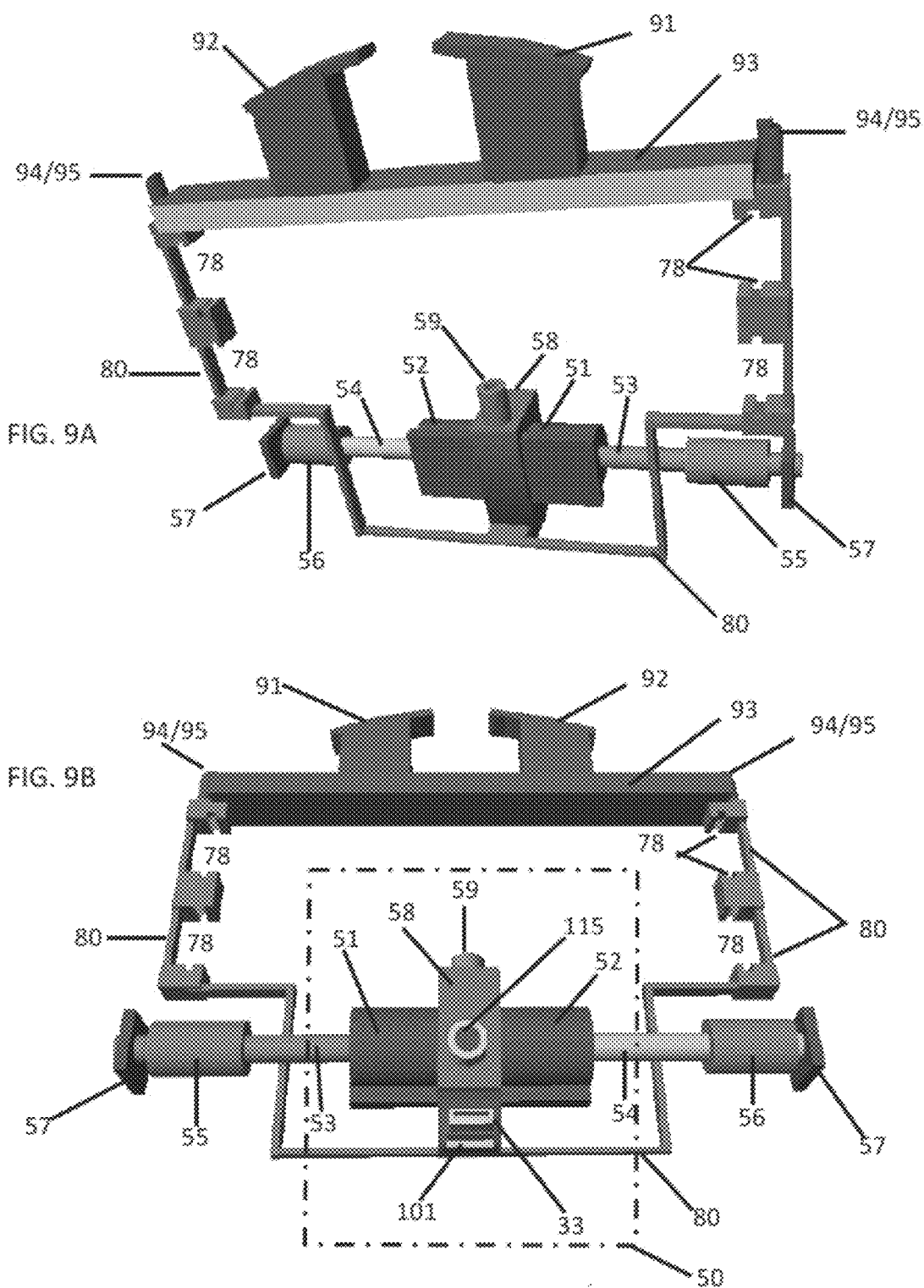
FIGS. 9A and 9B depict bottom and top views, respectively, of the electrical wiring harness connection of the sensors, UV light motion guides, and the main electromechanical subsystems of the exemplary sterilization system.

The Control Panel 110, as shown in FIG. 5B, is located on the Top Surface 31 of the Top Cover 30 of the Sterilization system 10. The Control Panel 110 has a Screen 111 to present text and graphic data about the status of the Sterilization system's 10 systems. The Control Panel 110 also has Selector Buttons 113 to scroll through data on the Screen 111 as well as to make selections in the control and programming of the Sterilization system 10. The Control Panel 110 also has one or more Status Indicators 112 to highlight important conditions within the operations of the Sterilization system 10. The Pass Through Port 32 in the Top Cover 30 allows access to the On-Off Button 115 which is directly attached to the Motion Control Management System 50 as shown in FIG. 9B. This allows the powering up or powering down of the Sterilization system 10 even when the Top Cover 30 is removed from the Sterilization system 10.

The Front 11 of the Main Body 20 of the Sterilization system 10 has the main Sensors 90 which are used to detect the presence of Biological Contaminants 137 and guide the Sterilization system 10 to the proper location to utilize its Main UV Lighting Components 60 to eradicate the Biological Contaminants 137. The Main UV Lighting Components 60 are located on the Bottom Surface 21 of the Main Body 20 of the Sterilization system 10. The Sterilization system 10 via the Computer core 58, as seen in the exploded view in FIG. 3, utilizes the data from the Sensors 90 to drive the Wheels 40 on the Bottom Surface 21 of the Main Body 20 of the Sterilization system 10 so that the Main UV Lighting Components 60 on the Bottom Surface 21 of the Main Body 20 can be activated to eradicate the Biological Contaminants 137 on Surfaces 130 over which the Sterilization system 10 travels. Wheels 40 are driven independently by commands from the Computer Core 58 via two different drive motors, the Left Wheel Drive Motor 51 and the Right Wheel Drive Motor 52. Each motor (51 and 52) is connected to its own drive shaft, Left Drive Shaft 53 and Right Drive Shaft 54 which are in turn independently connected to the drive drums, Left Drive Drum 55 and Right Drive Drum 56, by a friction drive of direct contact of the Drive Drums 55/56 against Wheels 41/42. The drive drums are in contact with the wheels 40 through the left and right Wheel Wells 25. The Wheel Wells 25 extend from the Bottom Surface 21 of the Main Body 20 through to the Top Surface 22 of the Main Body 20 as shown in FIGS. 4A and 4B. This enables the independent Drive Motors 51 and 52 to spin their independent Drive Shafts 53 and 54 which turn the independent Drive drums 55 and 56 against the Wheels 41 and 42 so that the difference in speed or direction of either of the Wheels 40 can be independently controlled for highly accurate motion and steering of the Sterilization system 10. The two wheels 41 and 42 are aided in the steering of the Sterilization system 10 by the front Steering Ball 43 which sits in its own Ball Cavity 24 at the front end of the Main Body 20. The Ball Cavity 23 holds the Steering Ball 43 in position by its rounded and tapered interior contour which allows the bottom of the Steering ball 24 to protrude from the bottom Surface 21 of the Main Body 20 through Ball Cavity 23 without falling out of the bottom of the Ball Cavity 23. Additionally, from above the Ball Cavity 23 holds the Steering Ball 43 in position against the surface 130 below the bottom Surface 21 of the Main Body 20 via the pressure of the Ball Cavity Cover 45 (as shown in exploded view FIG. 3 and FIG. 6.) which fits into the Top Surface 22 opening of Ball Cavity 23 and retains Steering Ball 43 in a proper position so that Steering Ball 43 acts as the front omnidirectional rolling pivot ball which allows the Sterilization system 10 to move precisely on a path designated by the Computer Core 58.

Figure 8:
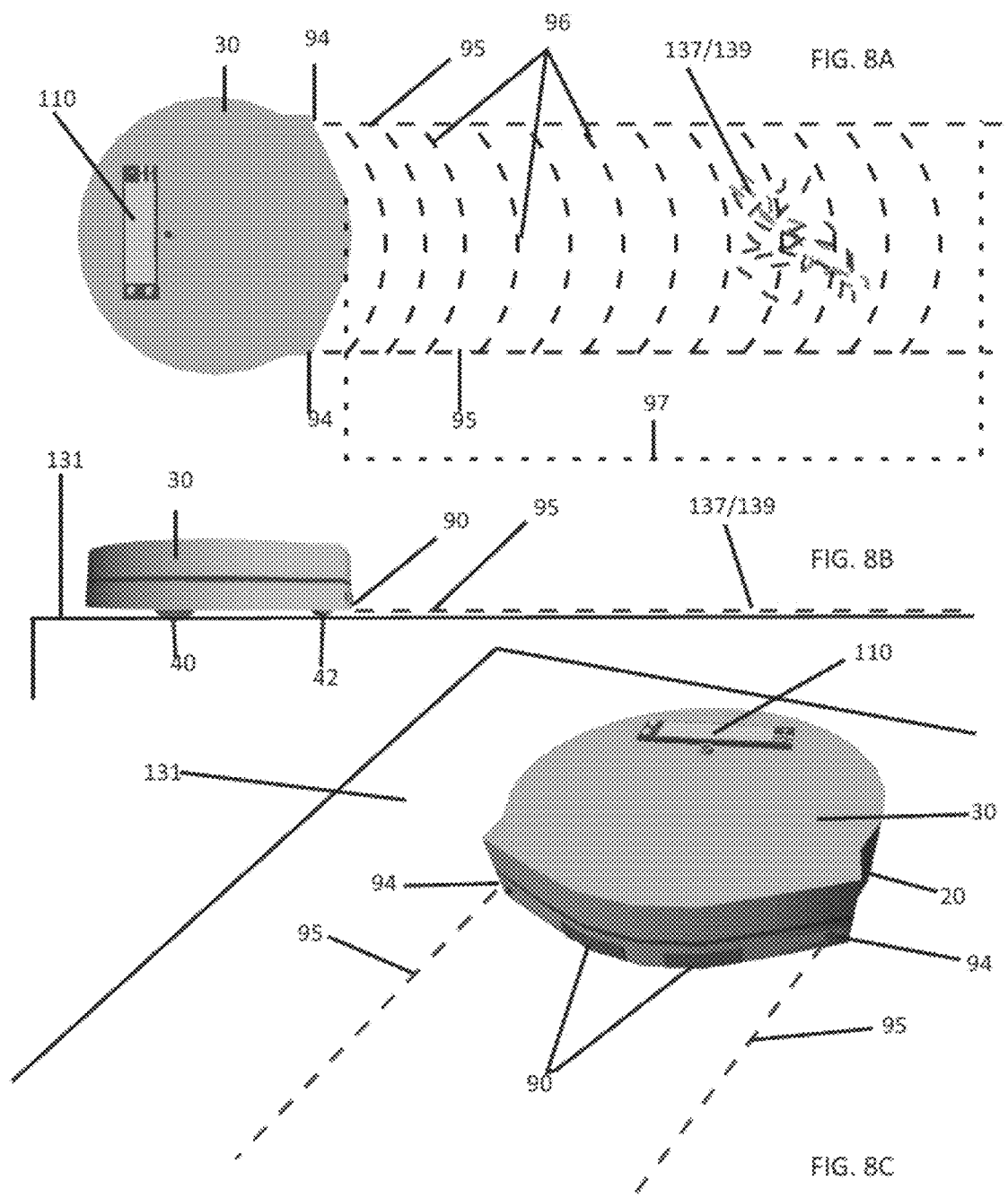
FIGS. 8A and 8B depict top, side, and perspective views, respectively, of the exemplary sterilization system showing navigation components and sensor use in the location of biological microorganisms.

As seen in FIG. 2A and 2B, and illustrated in FIG. 8A, the Sterilization system 10 can include two forward looking sensors/illuminators 91/92 which emit a Low Level UV Forward Projected Light 97 and then, using the Computer Core 58 of the Sterilization system 10, reads the presence of Biological Contaminants 137 by detecting the Illumination 138 of the Biological Contaminants 137 when they are struck by the Low Level UV Forward Projected Light 97. It is noted that each of components 91/92 could include an illuminator (such as a UV light or other light emitter to be directed at surfaces) as well as a sensor, or one of 91/92 could be a sensor and the other of 91/92 could be an illuminator. If another light emitter positioned elsewhere on the Sterilization system 10 is to be used to shine light (e.g., UV light, black light, etc.) at biological contaminants (for detection of the illumination/fluorescence of the contaminants or other features of the appearance of the contaminants under various lights), then both of 91/92 may be sensors. One or more sensors/illuminators can be positioned anywhere deemed appropriate on the Sterilization system 10. Contaminants 137 (particularly biological contaminants) are expected to Illuminate/Fluoresce 138 (or have another characteristic appearance on a surface such that portions of a surface with contaminants vary in appearance from portions of the surface without the same contaminants) when illuminated by Ultra Violet (UV) Light Projection 63 (or projections of other lights). The Sterilization system 10 utilizes the interaction of Biological Contaminants 137 and Ultra Violet (UV) Light Projection 63 to act as a target designator to generate navigational commands for the Sterilization system 10 and institute eradication protocols within the Computer Core 58 of the Motion Management System 50 of Sterilization system 10.

As seen in FIG. 2A The Bottom Surface 21 of the Main Body 20 houses the Main Lighting Components 60 which are composed of two different sets of UV lights. These are the Stationary UV Bulbs 61 and the Movable UV Bulbs 62. Both sets of Main Lighting Components 60 are capable of emitting a UV Light Projection 63 capable of the eradication of Biological Contaminants 137. The Stationary UV Bulbs 61 are mounted in a set of recessed Cavities 28 within the structure of the Bottom Surface 21 of the Main Body 20 of the Sterilization system 10. The Movable UV Bulbs 62 are mounted in a set of recessed Cavities 29 within the structure of the Bottom Surface 21 of the Main Body 20 of the Sterilization system 10. At each end the Movable UV Bulbs 62 are mounted to the Riser Guides 76 which are connected to the UV Height Management System 70 that is located on the Top Surface 22 of the Main Body 20 of the Sterilization system 10. The UV Height Management System 70 adjusts the height of the Movable UV Bulbs 62 in reference to their proximity to the Surfaces 130 beneath the Sterilization system 10. The location guidance for the vertical motion of the UV Height Management System 70 and in specific the Riser Guides 76 holding the Movable UV Bulbs 62 are the Riser Guide Sensor Slots 78. The Riser Guide Sensor Slots 78 are part of the Wiring Harness 80 which distributes power to the various powered components of Sterilization system 10, such as the Forward Looking Sensors/Illuminators 91/92, the Downward Looking Sensor 93, the Laser Range Finder 94 and Laser Path Indicator 95. The Riser Guide Sensor Slots 78 on the Wiring Harness 80 track the relative motion of the Riser Guides 76 as they pass up and down through the Riser Guide Sensor Slots 78. The monitoring of the Riser Guides 76 in the Riser Guide Sensor Slots 78 can be via a simple motion sensor using magnetics, optics, even dimples tripping a micros switch, or other motion tracking technology. The Computer Core 58 utilizing the data from the Riser Guide Sensor Slots 78 can accurately position the Movable UV Bulbs 62 for maximum effective use. The Computer Core 58 may have a simple logic system to determine the optimal use of onboard energy, as it is applied towards locomotion, Sensors 90 and the intensity of UV Light Projection 63 to accomplish maximum eradication of Biological Contaminants 137 on Surfaces 130. When energy reserves are deemed too low to continue safely, the Sterilization system 10 could return to its charging dock where a physical connection or induction charging system would reenergize the Battery 100 of the Sterilization system 10.

The movement of the Movable UV Bulbs 62 closer to the Floor 131 beneath its Bottom Surface 21 will increase the amount of UV radiation which will impact any Biological Contaminants 137 beneath the Sterilization system 10. As seen in FIG. 7, the Base Gap 141 beneath Movable UV Bulbs 62 when fully recessed into the Bottom Surface 21 of the Sterilization system 10 is much greater than the Base gap 141 when the Movable UV Bulbs 62 are in their lower position as shown in FIG. 7B. This ability to Lower the UV Lights 143 and change the height of the UV lights is one of several operational methodologies which can be employed by the Sterilization system 10 to provide the best eradication of Biological Contaminants 137 on surfaces beneath the Sterilization system 10.

Figure 3:
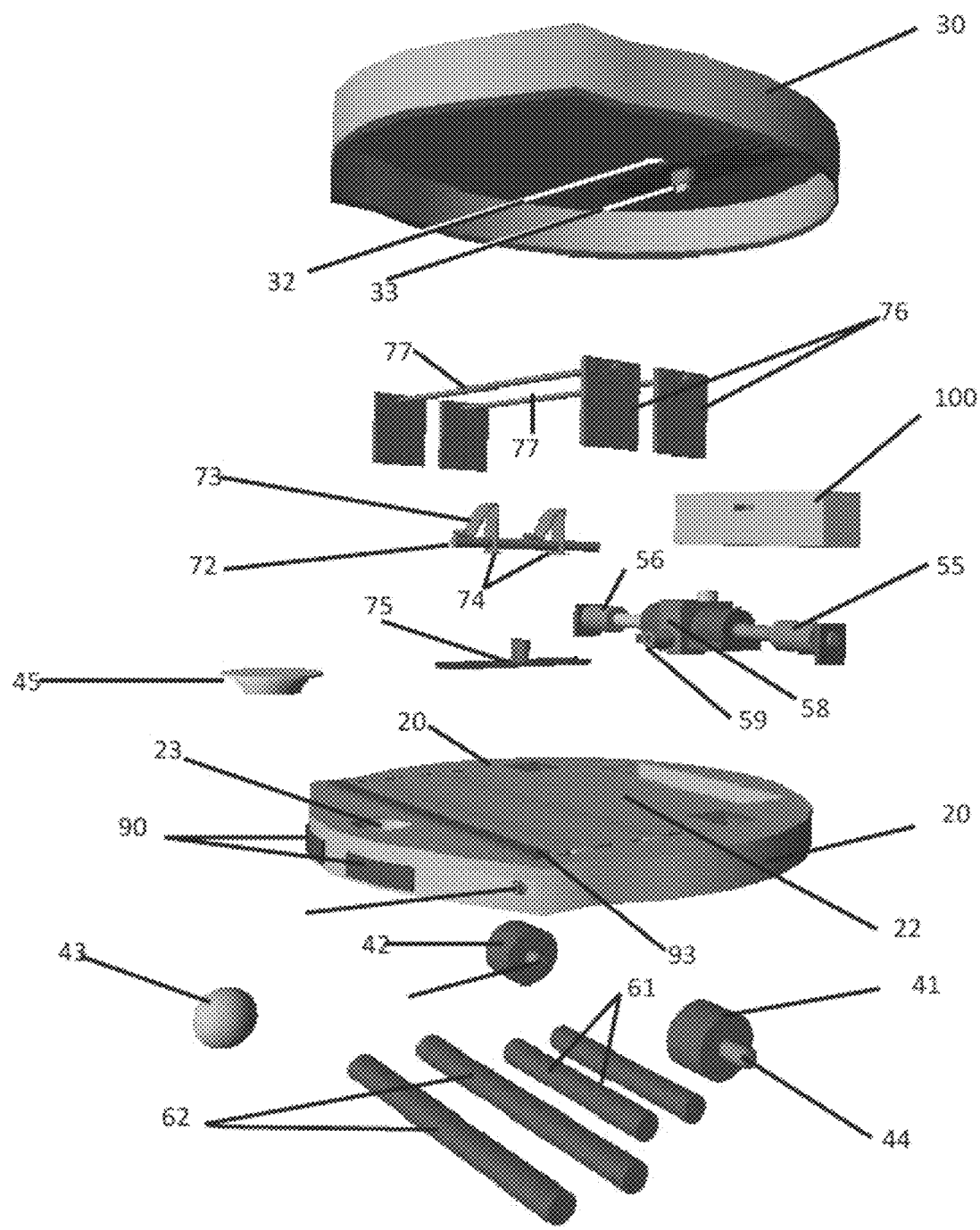
FIG. 3 depicts an exploded view of the sub-components of the exemplary sterilization system.
Figure 4:
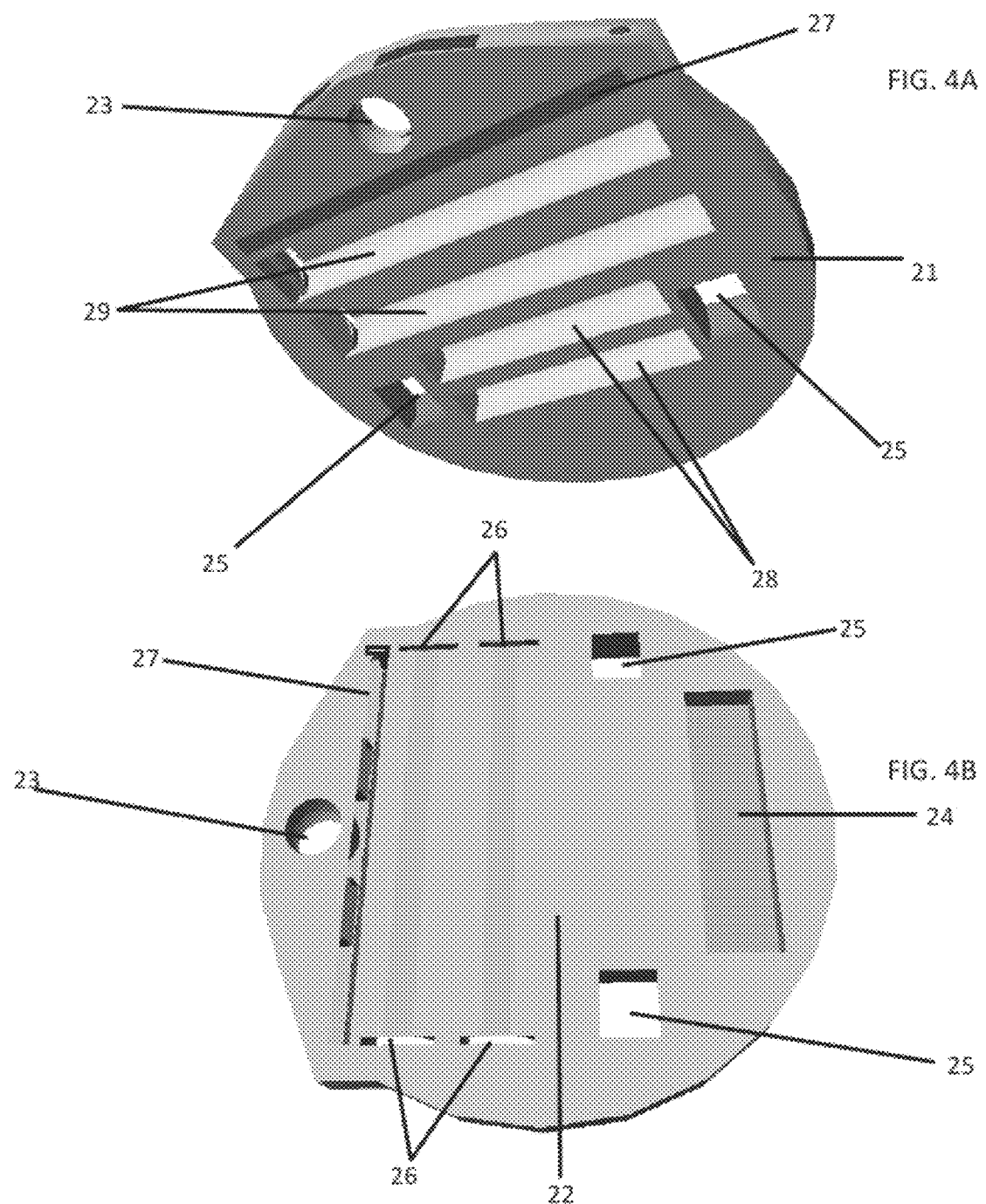
FIGS. 4A and 4B depict perspective views of the bottom and top, respectively, of a main body of the exemplary sterilization system without sub-components.

Although several methods to raise 142 and lower 143 the Movable UV Bulbs 62 can be used, the method shown in this version utilizes a graduated Height Ramp 73 as shown in both the exploded view of FIG. 3 and the two illustration of FIGS. 6A and 6B. The Height Ramps 73 are mounted on a Height Piston 72 which moves in a linear fashion which is parallel with the direction from the front 11 to back 12 of the Main Body 20 of the Sterilization system 10. The Height Ramps 73 on the Height Piston 72 ride in a Guide Track 75 which maintains a constant linear direction for the motion of the Height Piston 72. The Height Piston 72 is inserted into the Piston Port 71 of the Step Motor 59 of the Motion Management System 50 as shown in FIGS. 6A and 6B, as well as in FIG. 9B. The UV Height Management System 70 utilizes the Step Motor 59 to create a front 11 to back 12 pushing and pulling motion on the Height Piston 72 when instructed by the Computer Core 58 in response to Sensor 90 data regarding the level of Illumination 138 from Biological Contaminants 137 which are coming under the Bottom Surface 21 of the Sterilization system 10.

The Movable UV Bulbs 62 are attached to a set of Riser Guides 76 which extend through the Top Surface 22 of the Main Body 20 and come out at each end of the Cavity 29 on the Bottom Surface 21 of the Sterilization system 10. Each of the Movable UV Bulbs 62 is held between a set of the Riser Guides 76 which are perpendicular to the end of the Movable UV Bulbs 62. The Riser Guides 76 are parallel with the Height Ramps 73 on the Top Surface 22 of the Main Body 20. At the top of each set of Riser Guides 76 (above the Top Surface 22 and above each Movable UV Bulb 62), a single shaft, the Riser Rod 77, connects the two Riser Guides 76 on each end of the Movable UV Bulbs 62 so that each Movable UV Bulb 62 is held locked between the Riser Guides 76 at the bottom and has a Riser Rod 77 directly above it and above the Top Surface 22 of the Main Body 20. As shown in FIGS. 6A and 6B, the two Riser Rods 77 (above the two Movable UV Bulbs 62) are in contact with the slanted surfaces of the Height Ramps 73. The front to back linear motion of the Height Piston 72 changes the position of the Height Ramps 73 and in-turn causes the Riser Rods to either raise or lower the Riser Guides 76 due to the change in the position of the Riser Rods 77 on the slanted surface of the Height Ramps 73. The motion of the Height Piston 72 thus causes the Movable UV Bulbs 62 to either be raised or lowered. The activation of the Step Motor 59 which causes the linear motion of the Height Piston 72 and in-turn the vertical positioning of the Movable UV Bulbs 62 is regulated by the Sensor Data 98 received from the Sensors 91/92 and interpreted by Computer Core 58 of the Sterilization system 10.

The higher the level of Illumination 138 the less of a Base Gap 141 may be allowed between the Movable UV Bulbs 62 and the Biological Contaminants 137 (assuming the Movable UV Bulbs 62 is not prohibited by, for example, thick carpeting or other objects). In this way the most intense UV light radiation can be brought to bear upon the Biological Contaminants 137 to ensure their eradication by the UV Light Projection 63. To ensure that the cleansing process is complete, the Computer Core 58 can instruct the Motion Management system 50 to reverse the direction of the two Wheel Motors 51 and 52 so that the Sterilization system 10 backs up over the just previously cleaned area. The Downward Looking Sensor 93, as seen in FIGS. 2A, 9A and 9B, will then be able to detect any residual Illumination 138 from any non-eradicated Biological Contaminants 137 and will trigger a re-cleansing protocol within the Computer Core 58.

The Computer Core 58 may employ other eradication tactics in either the basic cleaning mode or a re-cleansing mode. The eradication protocols can be used independently of each other or in combination. Besides changing the proximity of the UV Moveable Bulbs 62, other methodologies that can be deployed by the Sterilization system 10 include [1] Computer core 58 control over the power levels to the Moveable Bulbs 62 and/or the Stationary UV Bulbs 61, and [2] Computer core 58 control over the speed and direction of the Sterilization system 10 movement over a particular Surface 130.

The Computer Core 58 in response to Sensor 90 feedback from Forward Looking sensors 91/92 and/or Downward Looking Sensor 93 may change the height adjustment of the UV Height Management System 70, or energize one or more of the Main UV Lighting Components 60 with a higher power level to boost the UV's ability to eradicate the Biological Contaminants 137. The re-cleansing protocol may also change the speed at which the Sterilization system 10 will move over the Biological Contaminants 137. In this way the "time on target" can be maximized to allow a better chance of complete eradication of the Biological Contaminants 137 within a minimum number of passes of the Sterilization system 10 over the Biological Contaminants 137 to be eradicated.

Figure 10:
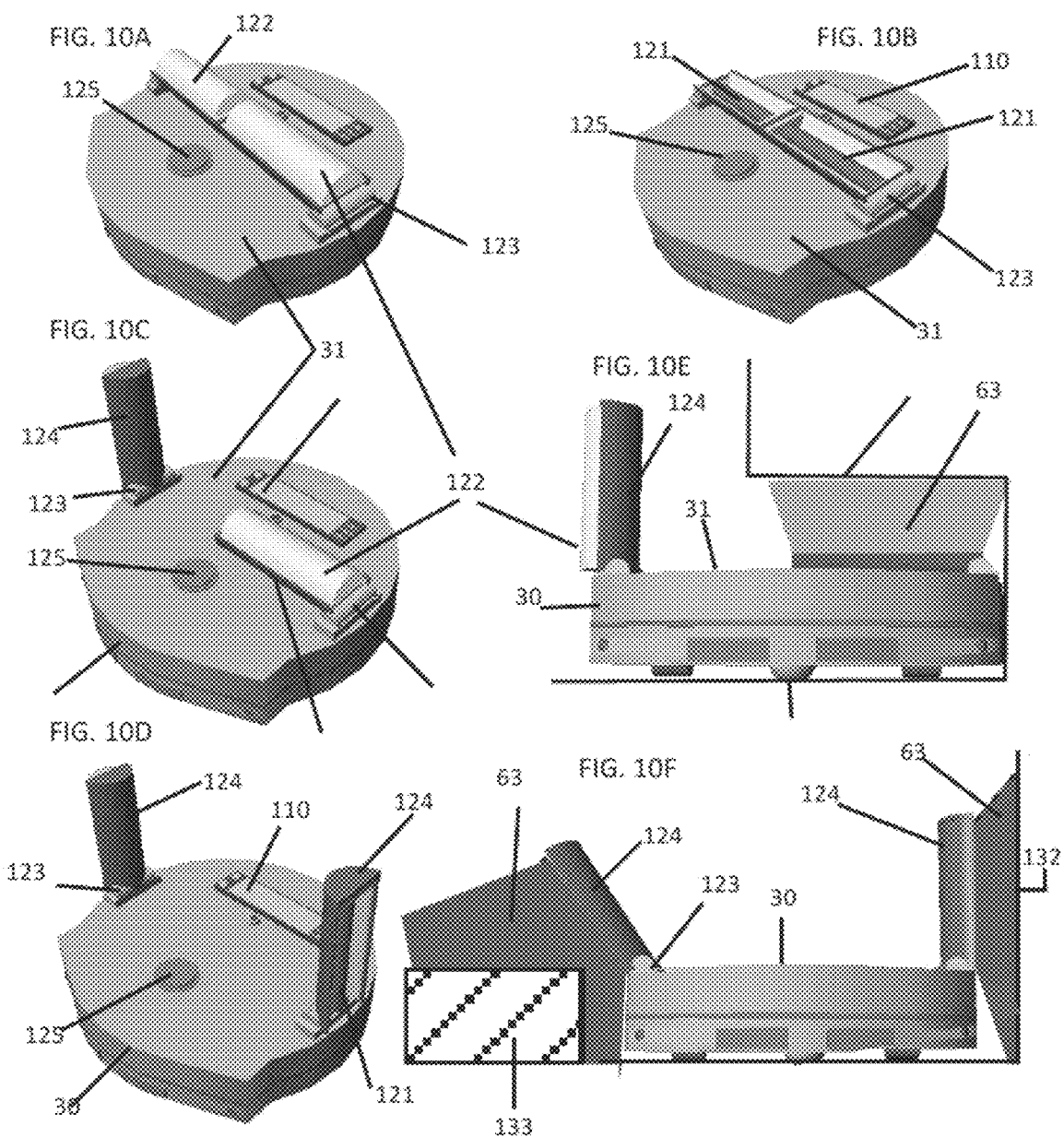
FIG. 10A depicts a top perspective view of an alternative exemplary sterilization system with an Auxiliary Lighting System in its stowed and non-operational position.
FIG. 10B depicts a top perspective view of the alternative exemplary sterilization system with both units of the Auxiliary Lighting System in a lowered but deployed and operational position.
FIG. 10C depicts a top perspective view of the alternative exemplary sterilization system with a first unit of the Auxiliary Lighting System in its stowed and non-operational position and a second unit in an upright deployed and operational position.
FIG. 10D depicts a top perspective view of the alternative exemplary sterilization system with both units of the Auxiliary Lighting System in an upright deployed and operational position.
FIG. 10E depicts a front view of the alternative exemplary sterilization system with one unit of the Auxiliary Lighting System in a down but deployed and UV emitting operational position and the second unit in an upright but non-deployed position.
FIG. 10F depicts a front view of the alternative exemplary sterilization system with the first unit of the Auxiliary Lighting System in an upright UV emitting operational position and the second unit in an upright angled deployed UV emitting operational position.

Referring to FIGS. 10A-10F, the Sterilization system 10 can alternatively or additionally include an additional Auxiliary Light System 120 mounted on the Top Surface 31 of the Top Cover 30. This Sterilization system 10 has enhanced capabilities in both floor and adjacent object scanning and biological contaminant eradication systems. The addition of the Top Mounted UV Bulbs 121 allows the Sterilization system 10 to use its UV Light Projection 63 to irradiate objects above the Floor 131 line and address Vertical Edges 134, as shown in FIG. 10F, which can be the base of a Wall 132 or the vertical edge 134 and Horizontal Surface 135 that make up the corner of a Gym Mat 133. Additionally as shown in FIG. 10E, the use of the Auxiliary Light System 120 in a configuration in which one or more of the Top Mounted UV Bulbs 121 are pointed upward from the Top Surface 31 of the Top Cover 30 of the Sterilization system 10 allowing the UV Light Projection 63 to be aimed at the underside or a Tilted Surface 136 above the Sterilization system 10. As shown in FIGS. 10A and 10C, the Auxiliary Light System 120 has its Top Mounted UV Bulbs 121 secured within Bulb Support Structures 124 which are on Motorized Pivots 123 attached to the Top Surface 31 of the Top Cover 30 of the Sterilization system 10. The Top Mounted UV Bulbs 121 inside the dual Bulb Support Structures 124 which have Rotational Shields 122, as shown in FIG. 10A, and are in their lowered and most compact position laying flat on the Top Surface 31 of the Top Cover 30 of Sterilization system 10.

As shown in FIG. 10B, the Rotational Shields 122 of both Bulb Support Structures 124 on the Top Surface 31 of the Top Cover 30 are rotated so that the Top Mounted UV Bulbs 121 are visible and both available for UV Light Projection 63, if commanded to do so by the Computer Core 58. In FIG. 10C the Sterilization system 10 has one Bulb Support Structure 124 in an upright position having been rotated upward by the Motorized Pivot 123 at the base of the Bulb Support Structures 124 on the command of the Computer Core 58. An Upward looking Sensor 125 is part of the features of the Secondary Embodiment and is shown on the on the Top Surface 31 of the Top Cover 30. The Upward looking Sensor 125 will sense the above Sterilization system 10 space to let the Computer Core 58 know about obstructions and undercuts in the path of the Sterilization system 10 which may affect the use of the Auxiliary Light System 120, or actually "impact" the Auxiliary Light System 120 components in a damaging way. In FIG. 10D the Sterilization system 10 is shown with both Bulb Support Structures 124 rotated by their respective Motorized Pivots 123 into full upright position on the Top Surface 31 of the Top Cover 30. One Bulb Support Structures 124 has its Rotational Shield 122 in an open position while the other Bulb Support Structures 124 as its Rotational Shield 122 in a closed position. The multiple configuration capability of this version provides operational flexibility to the Sterilization system 10.

The following tables provide information on the quantity of UV light that would be expected to kill particular biological contaminants. The sterilization system can be pre-programmed with various "kill profiles" for use when particular contaminants are being targeted or depending on how contaminated an area is expected to be. For example, profiles may tend towards greater times of exposure depending on the level or type of contamination anticipated for an area or during a time period.

| Organisms: | pW-sec/cm$^2$ 90% Eliminated |
|---|---|
| BACTERIA | |
| Bacillus anthracis - Anthrax | 4,520 |
| Bacillus anthracis spores - Anthrax spores | 24,320 |
| Bacillus magaterium sp. (spores) | 2,730 |
| Bacillus magaterium sp. (veg.) | 1,300 |
| Bacillus paratyphusus | 3,200 |
| Bacillus subtilis spores | 11,600 |
| Bacillus subtilis | 5,800 |
| Clostridium tetani | 13,000 |
| Corynebacterium diphtheria | 3,370 |
| Ebertelia typhosa | 2,140 |
| Escherichia coli | 3,000 |
| Leptospiracanicola - infection Jaundice | 3,150 |
| Micrococcus candidus | 6,050 |
| Micrococcus sphaeroides | 1,000 |
| Mycobacterium tuberculosis | 6,200 |
| Neisseria catarrhalis | 4,400 |
| Phytomonas tumefaciens | 4,400 |
| Proteus vulgaris | 3,000 |
| Pseudomonas aeruginosa | 5,500 |
| Pseudomonas fluorescens | 3,500 |
| Salmonella enteritidis | 4,000 |
| Salmonela parathphi - Enteric fever | 3,200 |
| Salmonella thyphosa - Typhoid fever | 2,150 |
| Salmonella typhimurium | 8,000 |
| Sarcina lutea | 19,700 |
| Serratia marcescens | 2,420 |
| Shigella dyseteriae - Dysentery | 2,200 |
| Shigella flexneri - Dysentery | 1,700 |
| Shigella paradysentariae | 1,680 |
| Spirillum rubrum | 4,400 |
| Staphylococcus albus | 1,840 |
| Staphylococcus aerius | 2,600 |
| Staphylococcus hemolyticus | 2,160 |
| Staphylococcus lactis | 6,150 |
| Streptococcus viridans | 2,000 |
| Vibrio comma - Cholera | 3,375 |
| MOLD | |
| Aspergillius flavus | 60,000 |
| Aspergillius glaucus | 44,000 |
| Aspergillius niger | 132,000 |
| Mucor racemosus A | 17,000 |
| Mucor racemosus B | 17,000 |
| Oospora lactis | 5,000 |
| Penicillium expansum | 13,000 |
| Penicillium roqueforti | 13,000 |
| Penicillium digitatum | 44,000 |
| Rhisopus nigricans | 111,000 |

-continued

| PROTOZOA | |
|---|---|
| *Chlorella Vulgaris* | 13,000 |
| Nematode Eggs | 4,000 |
| Paramecium | 11,000 |
| VIRUS | |
| Bacteriopfage - *E. Coli* | 2,600 |
| Infectious Hepatitis | 5,800 |
| Influenza | 3,400 |
| Poliovirus - Poliomyelitis | 3,150 |
| Tobacco mosaic | 240,000 |
| YEAST | |
| Brewers yeast | 3,300 |
| Common yeast cake | 6,000 |
| *Saccharomyces carevisiae* | 6,000 |
| *Saccharomyces ellipsoideus* | 6,000 |
| *Saccharomyces spores* | 8,000 |

|  |  | Model | VH01-20.00 | VH03-200.0 | VH07-20.00 |
|---|---|---|---|---|---|
|  |  | Name | Large Wand | Small Wand | Bad Vacuum |
|  | Output | Waffs | 6 | 3 | 6 |
|  | Intensity | μW/cm2 | 2500 | 1200 | 6000 |
|  | Total Output | μW/Tfl. area | 18000 | 12225 | 528000 |
|  |  | Total emitting area | 72.00 | 10.19 | 88.00 |
|  | μW/cm2 |  | Minutes for 90% Kill Rate | | |
| Typhoid | 2,150 | 1 Square cm | 0.01 | 0.03 | 0.01 |
| 72 | (18 cm × 4 cm) | Remote Control | 0.01 | 0.21 | N/A |
| 144 | (18 cm × 4 c × 2) | Telephone | 0.03 | 0.42 | N/A |
| 480 | (40 cm × 32 cm) | Toilet Seat | 0.10 | 1.41 | N/A |
| 2394 | (63 cm × 38 cm) | Queen Pillow | 0.48 | N/A | 0.16 |
| 9677 | (127 cm × 76 cm) | Baby Crib Mattress | 1.33 | N/A | 0.66 |
| 18909 | (191 cm × 99 cm) | Single Mattress | 3.76 | N/A | 1.28 |
| 26167 | (191 cm × 137 cm) | Double Mattress | 5.21 | N/A | 1.78 |
| 30856 | (203 cm × 152 cm) | Queen Mattress | 6.14 | N/A | 2.09 |
| 39179 | (203 cm × 193 cm) | King Mattress | 7.80 | N/A | 2.66 |
| Influenza | 3,400 | 1 Square cm | 0.02 | 0.05 | 0.01 |
| 72 | (18 cm × 4 cm) | Remote Control | 0.02 | 0.33 | N/A |
| 144 | (18 cm × 4 c × 2) | Telephone | 0.05 | 0.67 | N/A |
| 480 | (40 cm × 32 cm) | Toilet Seat | 0.15 | 2.22 | N/A |
| 2394 | (63 cm × 38 cm) | Queen Pillow | 0.75 | N/A | 0.26 |
| 9677 | (127 cm × 76 cm) | Baby Crib Mattress | 3.05 | N/A | 1.04 |
| 18909 | (191 cm × 99 cm) | Single Mattress | 5.95 | N/A | 2.03 |
| 26167 | (191 cm × 137 cm) | Double Mattress | 8.24 | N/A | 2.81 |
| 30856 | (203 cm × 152 cm) | Queen Mattress | 9.71 | N/A | 3.31 |
| 39179 | (203 cm × 193 cm) | King Mattress | 12.33 | N/A | 4.20 |
| Hepatitus | 5,800 | 1 Square cm | 0.04 | 0.05 | 0.01 |
| 72 | (18 cm × 4 cm) | Remote Control | 0.04 | 0.57 | N/A |
| 144 | (18 cm × 4 c × 2) | Telephone | 0.08 | 1.14 | N/A |
| 480 | (40 cm × 32 cm) | Toilet Seat | 0.26 | 3.80 | N/A |
| 2394 | (63 cm × 38 cm) | Queen Pillow | 1.29 | N/A | 0.44 |
| 9677 | (127 cm × 76 cm) | Baby Crib Mattress | 5.20 | N/A | 1.77 |
| 18909 | (191 cm × 99 cm) | Single Mattress | 10.15 | N/A | 3.46 |
| 26167 | (191 cm × 137 cm) | Double Mattress | 14.05 | N/A | 4.79 |
| 30856 | (203 cm × 152 cm) | Queen Mattress | 16.57 | N/A | 5.65 |
| 39179 | (203 cm × 193 cm) | King Mattress | 21.04 | N/A | 7.17 |
| Anthrax | 4,520 | 1 Square cm | 0.03 | 0.06 | 0.01 |
| 72 | (18 cm × 4 cm) | Remote Control | 0.03 | 0.44 | N/A |
| 144 | (18 cm × 4 c × 2) | Telephone | 0.06 | 0.89 | N/A |
| 480 | (40 cm × 32 cm) | Toilet Seat | 0.20 | 2.96 | N/A |

| | | | | | |
|---|---|---|---|---|---|
| 2394 | (63 cm × 38 cm) | Queen Pillow | 1.00 | N/A | 0.34 |
| 9677 | (127 cm × 76 cm) | Baby Crib Mattress | 4.05 | N/A | 1.38 |
| 18909 | (191 cm × 99 cm) | Single Mattress | 7.91 | N/A | 2.70 |
| 26167 | (191 cm × 137 cm) | Double Mattress | 10.95 | N/A | 3.73 |
| 30856 | (203 cm × 152 cm) | Queen Mattress | 12.91 | N/A | 4.40 |
| 39179 | (203 cm × 193 cm) | King Mattress | 16.40 | N/A | 5.59 |
| Mold A - 5,000 | | 1 Square cm | 0.03 | 0.07 | 0.01 |
| 72 | (18 cm × 4 cm) | Remote Control | 0.03 | 0.49 | N/A |
| 144 | (18 cm × 4 c × 2) | Telephone | 0.07 | 0.98 | N/A |
| 480 | (40 cm × 32 cm) | Toilet Seat | 0.22 | 3.27 | N/A |
| 2394 | (63 cm × 38 cm) | Queen Pillow | 1.11 | N/A | 0.38 |
| 9677 | (127 cm × 76 cm) | Baby Crib Mattress | 4.48 | N/A | 1.53 |
| 18909 | (191 cm × 99 cm) | Single Mattress | 8.75 | N/A | 2.98 |
| 26167 | (191 cm × 137 cm) | Double Mattress | 12.11 | N/A | 4.13 |
| 30856 | (203 cm × 152 cm) | Queen Mattress | 14.28 | N/A | 4.87 |
| 39179 | (203 cm × 193 cm) | King Mattress | 18.14 | N/A | 6.18 |
| Dust Mite Eggs* 17,500 | | 1 Square cm | 0.12 | 0.24 | 0.05 |
| 2394 | (63 cm × 38 cm) | Queen Pillow | 3.88 | 57.12 | 1.32 |
| 9677 | (127 cm × 76 cm) | Baby Crib Mattress | 15.68 | 230.88 | 5.35 |
| 18909 | (191 cm × 99 cm) | Single Mattress | 30.64 | 451.13 | 10.45 |
| 26167 | (191 cm × 137 cm) | Double Mattress | 42.20 | 624.30 | 14.45 |
| 30856 | (203 cm × 152 cm) | Queen Mattress | 50.00 | 736.17 | 17.04 |
| 39179 | (203 cm × 193 cm) | King Mattress | 63.48 | 934.74 | 21.64 |

By reviewing the above the reader can see that various combinations of available features in the Sterilization system 10 can provide a highly advantageous system for the location and eradication of infectious bacterial and virus strains on floors, objects left on the floor and the low areas of walls, cabinets and angled structures like the tops and side edges of gym mats. The Sterilization system 10 can be physically operated using robotic components in an automated and programmable fashion and set about its task of cleansing a particular area of biological contaminants. Additionally, the enhanced "seek and destroy" capability provided by the sensor system in combination with its computer core and drive system has the ability to sense, locate, navigate to, and destroy biological contaminants wherever the Sterilization system 10 encounters their presence. To maximize its ability to destroy biological contaminants in various environments, the Sterilization system 10 can utilize an ability to change the proximity of the UV lights to the target area, change the intensity of the energy input to the UV lights, and/or change its speed of motion and move in various directions to accomplish a goal of sufficient "time on target" to allow the UV lights to do their job of eradicating biological contaminants. The Sterilization system 10 takes advantage of the proven ability of UV light to eradicate biological contaminants.

Various exemplary versions of the sterilization system may provide a self-propelled mobile platform utilizing one or more Ultra Violet light (UV) sources to eradicate biological contaminants on surfaces at which the UV light is directed. The self-propelled UV light source platform may control the energy intensity of the UV light emissions to increase or decrease the UV light's ability to eradicate biological contaminants on surfaces at which the UV light is directed. The self-propelled UV light source platform may be provided with the ability to change the physical separation distance between the UV light emission source and the physical location of the biological contaminants on a surface by moving the UV light source or the mobile platform to change the UV light's proximity to the biological contaminants in a manner which will increase or decrease the system's ability to eradicate biological contaminants on various surfaces at which the UV light is directed. The self-propelled UV light source platform may control the timing of the exposure of the UV light emissions to increase or decrease the UV light's ability to eradicate biological contaminants on surfaces at which the UV light is directed. The timing may be controlled by changing the speed at which the mobile platform travels over a surface, and/or the ability of the mobile platform to make repeated passes over a location for the purpose of increasing the time on target for the exposure of the UV light to the target biological contaminants.

Other exemplary versions of the sterilization system may include a self-propelled mobile platform utilizing one or more Ultra Violet light (UV) sources in combination with light sensors to detect biological contaminants on surfaces at which the UV light is directed via the detection of the visible fluorescence/illumination/change in appearance of the biological contaminants when irradiated by UV or other light. The self-propelled UV light source platform may use a photonic reaction in one or more light sensors mounted on the self-propelled UV light source platform to detect the illumination of the light-irradiated biological contaminants. The photonic reaction may suggest to the computer system of the self-propelled UV light source platform the presence of biological contaminants in a specific location in the proximity of the self-propelled UV light source platform. The illumination of the UV irradiated biological contaminants detected by light sensors mounted on the platform may create a target location for the computer guidance system of the self-propelled UV light source platform. Creation of a target location for the computer guidance system of the self-propelled UV light source platform may activate motion commands to the propulsion system of the self-propelled UV light source platform so that the platform can effectively navigate and move to the target location. Exemplary sterilization systems may alternatively or additionally one or more Ultra Violet light (UV) sources which are capable of projecting UV light at one or more locations in the proximity of the platform. The UV light sources can be directed at both the surface under the platform and at surfaces and objects next to and above the platform.

Various components of the sterilization system may be embodied in whole or in part within the circuitry of an application specific integrated circuit (ASIC) or a programmable logic device (PLD). Such components may be embodied in a computer understandable descriptor language which may be used to create an ASIC or PLD that operates as herein described.

It should also be understood that various terms referring to orientation and position are used throughout this document—for example, "top" (as in "light emitters on its top surface") and "bottom" (as in "extends from the bottom")—are relative terms rather than absolute ones. Moreover, it is to be understood that such terms as "forward," "rearward," "left," "right," "upwardly," "downwardly," and the like are words of convenience and are not to be construed as limiting terms. Thus, such terms should be regarded as words of convenience, rather than limiting terms.

It should be understood that the versions of the invention described above are merely exemplary, and the invention is not intended to be limited to these versions. Preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A self-propelled system for sterilizing surfaces, the system including:
   a. a robotic mobile platform having an ultraviolet light source, the robotic mobile platform being configured to neutralize biological contaminants by using the ultraviolet light source to emit ultraviolet light on a surface; and
   b. a controller interfaced with the ultraviolet light source,
      i. the controller being configured to control the ultraviolet light source so as to change a level of disinfection effected by the ultraviolet light source,
      ii. the level of disinfection being a percentage of biological contaminants neutralized on the surface on which the ultraviolet light is emitted; and
   c. a light sensor configured to detect illumination of biological contaminants irradiated with light;
   wherein the robotic mobile platform does not have a vacuum so as to avoid suction that could spread contagions or that could suck contagions into the robotic mobile platform.

2. The system of claim 1 wherein the controller is configured to vary an energy intensity of the ultraviolet light source to change levels of ultraviolet light being emitted on the surface based on at least one of:
   a. an amount of contamination anticipated for an area; and
   b. a type of biological contaminant anticipated for an area.

3. The system of claim 1 wherein the controller is further configured to vary a physical separation distance between the ultraviolet light source and a surface to change levels of ultraviolet light being emitted on the surface based on at least one of:
   a. an amount of contamination anticipated for an area; and
   b. a type of biological contaminant anticipated for an area.

4. The system of claim 3 wherein the physical separation distance is changed by moving the ultraviolet light source towards or away from a surface.

5. The system of claim 1 wherein the controller is further configured to change the level of disinfection by changing a time of exposure during which a surface is exposed to the ultraviolet light.

6. The system of claim 5 wherein:
   a. the robotic mobile platform is configured to travel over a surface as ultraviolet light is emitted on the surface; and
   b. the time of exposure is changed by changing a speed at which the robotic mobile platform travels over the surface.

7. The system of claim 5 wherein:
   a. the robotic mobile platform is configured to travel over a surface as ultraviolet light is emitted on the surface; and
   b. the controller is configured to change the time of exposure of the surface to ultraviolet light by instructing the robotic mobile platform to travel over at least a portion of the surface more than once.

8. The system of claim 1 wherein the controller is configured to:
   a. locate an illuminated portion of a surface; and
   b. emit ultraviolet light on the illuminated portion so as to neutralize biological contaminants located thereon.

9. The system of claim 8 further including a guidance system configured to control navigation of the robotic mobile platform over surfaces, wherein the guidance system is configured to navigate the robotic mobile platform to locate a portion of a surface that illuminates.

10. The system of claim 1 wherein the ultraviolet light source can be oriented to emit light:
    a. underneath the robotic mobile platform; and
    b. to a side of the robotic mobile platform beyond a perimeter thereof.

11. The system of claim 1 wherein ultraviolet light can be emitted from the robotic mobile platform in an upwardly direction away from a floor over which the robotic platform travels.

12. The system of claim 1 wherein the controller is further configured to adjust an orientation of the ultraviolet light source so as to target surfaces to the side of the robotic mobile platform, above the robotic mobile platform, and below the robotic mobile platform.

13. The system of claim 1 wherein:
    a. the robotic mobile platform is configured to move over surfaces; and
    b. the controller is configured to adjust a movement of the robotic mobile platform based on energy reserves available at the mobile platform so as to achieve neutralization of biological contaminants over an area before available energy reserves are depleted.

14. The system of claim 1 wherein the controller is further configured to control the ultraviolet source so as to vary the level of disinfection effected by the ultraviolet source based on a level of illumination detected by the light sensor.

15. A self-propelled system for sterilizing surfaces, the system including:
   a. a robotic mobile platform having an ultraviolet light source, the robotic mobile platform being configured to neutralize biological contaminants by using the ultraviolet light source to emit ultraviolet light on a surface;
   b. a light sensor configured to detect illumination of biological contaminants irradiated with light; and
   c. a controller interfaced with the ultraviolet light source, the controller being configured to:
      i. control the ultraviolet light source so as to change a level of disinfection effected by the ultraviolet light source, the level of disinfection being a percentage of biological contaminants neutralized on the surface on which the ultraviolet light is emitted;
      ii. emit ultraviolet light on a surface using the ultraviolet light source;
      iii. detect a level of illumination at an irradiated portion of the surface using the light sensor; and
      iv. compare the level of illumination detected by the light sensor with a threshold level of illumination, the threshold level corresponding with a level of biological contamination.

16. The system of claim 15 wherein illumination is detected via a photonic reaction in the light sensor, the light sensor being mounted on the robotic mobile platform.

17. A self-propelled system for sterilizing surfaces, the system including:
   a. a robotic mobile platform configured to travel over surfaces to be irradiated with ultraviolet light;
   b. an ultraviolet light source configured to emit ultraviolet light on a surface to neutralize biological contaminants;
   c. a light sensor configured to detect fluorescence of biological contaminants irradiated with ultraviolet light; and
   d. a controller configured to control the robotic mobile platform to irradiate surfaces using the ultraviolet light source based on fluorescence detected by the light sensor by adjusting one or both of:
      i. a path travelled by the robotic mobile platform; and
      ii. a speed at which the robotic mobile platform travels.

18. The system of 17 wherein:
   a. the light sensor detects the fluorescence of biological contaminants in the wake of the robotic mobile platform as the robotic mobile platform travels over a portion of a surface; and
   b. the controller is configured to travel over the portion of the surface a second time if the detected fluorescence exceeds a threshold level of fluorescence.

* * * * *